(12) United States Patent  (10) Patent No.: US 9,289,275 B2
Zhao et al.  (45) Date of Patent: Mar. 22, 2016

(54) BIONIC TOOTH IMPLANT, AND BASE AND SUB-ROOT THEREOF

(75) Inventors: Daguo Zhao, Chengdu (CN); Dazhang Wang, Chengdu (CN); Maosheng Su, Chengdu (CN); Guangda He, Chengdu (CN); Guosheng Liu, Chengdu (CN)

(73) Assignee: Daguo Zhao, Chengdu (CN)

( * ) Notice: Subject to any disclaimer, the term of this patent is extended or adjusted under 35 U.S.C. 154(b) by 41 days.

(21) Appl. No.: 13/880,727

(22) PCT Filed: Oct. 20, 2011

(86) PCT No.: PCT/CN2011/081001
§ 371 (c)(1),
(2), (4) Date: Apr. 20, 2013

(87) PCT Pub. No.: WO2012/051949
PCT Pub. Date: Apr. 26, 2012

(65) Prior Publication Data
US 2013/0288201 A1   Oct. 31, 2013

(30) Foreign Application Priority Data
Oct. 21, 2010  (CN) .......................... 2010 1 0514066

(51) Int. Cl.
*A61C 8/00*   (2006.01)
(52) U.S. Cl.
CPC ............... *A61C 8/0036* (2013.01); *A61C 8/001* (2013.01); *A61C 8/0025* (2013.01); *A61C 8/0043* (2013.01)
(58) Field of Classification Search
CPC ... A61C 8/0025; A61C 8/0043; A61C 8/0068
USPC .......................................... 433/172–176, 220
See application file for complete search history.

(56) References Cited

U.S. PATENT DOCUMENTS 3,474,537 A    10/1969  Christensen
3,579,831 A *   5/1971  Stevens et al. ................ 433/174
(Continued)

FOREIGN PATENT DOCUMENTS

CN       1163743 A     11/1997
CN    101249023 A      8/2008
(Continued)

*Primary Examiner* — Cris L Rodriguez
*Assistant Examiner* — Matthew Saunders
(74) *Attorney, Agent, or Firm* — Mei & Mark LLP

(57) ABSTRACT

The invention discloses a bionic tooth implant, comprising a main root and a basal platform, wherein the main root comprises a fixing root part positioned at the lower part thereof and a basal platform positioned at the upper part thereof; the bionic tooth implant also comprises at least one subsidiary root; the basal platform is mounted on the main root via the basal platform of the main root, wherein an inclined hole is provided on the basal platform; an inclined-direction hole communicated with the inclined hole is provided on the main root; the subsidiary root comprises the fixing root part positioned at the lower part thereof and a connected part positioned at the upper part thereof; the connected part is mounted in the inclined hole; the subsidiary root extends from the inclined-direction hole through the main root; and at least a part of the fixing root part is positioned at the outer part of the main root. As to the bionic tooth implant, after the main root is implanted into the jaw of the patient, the basal platform is directly inserted into the main root and then the matched installation between the main root and the basal platform is completed. The subsidiary root is directly screwed into the jaw and the whole implanting process of the bionic tooth implant is completed, without two-stage operation and the arrangement of the basal platform. The whole operation process is convenient and rapid.

20 Claims, 8 Drawing Sheets

(56) References Cited

U.S. PATENT DOCUMENTS

| | | | |
|---|---|---|---|
| 3,790,507 A | | 2/1974 | Hodosh |
| 3,955,280 A | * | 5/1976 | Sneer ............................. 433/169 |
| 4,960,381 A | | 10/1990 | Niznick |
| 5,026,285 A | * | 6/1991 | Durr et al. ..................... 433/173 |
| 5,076,788 A | | 12/1991 | Niznick |
| 5,246,370 A | * | 9/1993 | Coatoam ........................ 433/173 |
| 5,281,140 A | | 1/1994 | Niznick |
| 5,302,127 A | * | 4/1994 | Crisio, Jr. ....................... 433/173 |
| 5,542,847 A | * | 8/1996 | Margulies ....................... 433/173 |
| 5,564,925 A | | 10/1996 | Shampanier |
| 5,588,838 A | | 12/1996 | Hansson et al. |
| 5,890,902 A | | 4/1999 | Sapian |
| 5,947,733 A | | 9/1999 | Grande et al. |
| 5,984,681 A | | 11/1999 | Huang |
| 6,083,004 A | | 7/2000 | Misch et al. |
| 6,280,194 B1 | * | 8/2001 | Bjorn et al. ..................... 433/174 |
| 6,537,069 B1 | | 3/2003 | Simmons, Jr. |
| 6,663,388 B1 | | 12/2003 | Schar et al. |
| 7,108,510 B2 | | 9/2006 | Niznick |
| 7,160,109 B2 | | 1/2007 | Gervais |
| 7,249,949 B2 | | 7/2007 | Carter |
| 7,338,286 B2 | | 3/2008 | Porter et al. |
| 7,484,959 B2 | | 2/2009 | Porter et al. |
| 7,806,693 B2 | | 10/2010 | Hurson |
| 8,408,904 B2 | * | 4/2013 | Purga et al. .................... 433/173 |
| 8,591,513 B2 | * | 11/2013 | Overes et al. ................... 606/64 |
| 2003/0194679 A1 | * | 10/2003 | Odrich et al. .................. 433/173 |
| 2005/0107791 A1 | * | 5/2005 | Manderson ..................... 606/62 |
| 2006/0121417 A1 | * | 6/2006 | Scommegna et al. ......... 433/173 |
| 2006/0189991 A1 | * | 8/2006 | Bickley ............................ 606/72 |
| 2006/0246397 A1 | * | 11/2006 | Wolf ............................... 433/173 |
| 2008/0118892 A1 | | 5/2008 | Adams |
| 2008/0124675 A1 | | 5/2008 | Adams |
| 2008/0233538 A1 | * | 9/2008 | Hug et al. ....................... 433/174 |
| 2009/0258329 A1 | | 10/2009 | Adams |
| 2010/0055646 A1 | * | 3/2010 | Zhao ............................... 433/174 |
| 2010/0196850 A1 | * | 8/2010 | Konig ............................. 433/173 |
| 2010/0196851 A1 | * | 8/2010 | Konig ............................. 433/173 |
| 2011/0117522 A1 | | 5/2011 | Verma et al. |
| 2011/0137312 A1 | * | 6/2011 | Mantovani et al. ............. 606/63 |
| 2011/0282398 A1 | * | 11/2011 | Overes et al. ................... 606/304 |

FOREIGN PATENT DOCUMENTS

| | | | |
|---|---|---|---|
| CN | 101357079 A | | 2/2009 |
| CN | 101357079 | * | 7/2010 |
| CN | 101947139 A | | 1/2011 |
| JP | 11-318942 A | | 11/1999 |
| JP | 2000-60872 A | | 2/2000 |
| JP | 2000-060872 A | | 2/2000 |
| WO | WO 03088862 A1 | * | 10/2003 |

* cited by examiner

BIONIC TOOTH IMPLANT, AND BASE AND SUB-ROOT THEREOF

This is a §371 National Stage application of PCT/CN2011/081001, filed Oct. 20, 2011, which claims the benefit of priority of Chinese Application 201010514066.4, filed Oct. 21, 2010, both of which are incorporated herein by reference.

TECHNICAL FIELD OF THE INVENTION

The invention relates to the improvement of a structure of a bionic tooth implant and, more specifically, to a bionic tooth implant as well a basal platform and a subsidiary root thereof.

TECHNICAL BACKGROUND OF THE INVENTION

The invention is based on the improvement of China's invention patent 200710048850.9. China's invention patent 200710048850.9 discloses a bionic tooth implant. The bionic tooth implant comprises a fixed root part, a neck part and a basal platform part. The fixed root part comprises a main root and at least one subsidiary root. The diameter of the subsidiary root is smaller than that of the main root. An inclined hole passes through from the main root or the neck to the outer periphery thereof, or the inclined hole passes through from the main root or the neck to the outer periphery thereof at the same time. The upper end part of each subsidiary root is provided obliquely in one inclined-direction hole. The invention has great early stable performance and early anti-rotation torsionproof capability, may increase contact area between the implant and the jaw, improves successful rate of immediate implant and immediate stress, and strengthens successful rate effectively playing a chewing role for a long time.

Although the above invention has proposed the form of the multi-root bionic tooth implant but its structure, basal platform and subsidiary root need to be improved, so that the surgeon may smoothly implement simple and rapid installation operation in the narrow human mouth cavity environment.

SUMMARY OF THE INVENTION

As to the problem that the bionic tooth implant of the prior art may not quickly and accurately be positioned and placed during installation, the invention proposes an improved structure of a bionic tooth implant as well as a basal platform and a subsidiary root thereof. As the basal platform and subsidiary root of the bionic tooth implant has simple structure which may rapidly be mounted, the practical value where the bionic tooth implant may be operated in the human mouth cavity may be improved.

In order to achieve the abovementioned objective, the invention adopts the following technical proposal:

A bionic tooth implant, comprising a main root and a basal platform, wherein the main root comprises a fixing root part positioned at the lower part thereof and a basal platform part positioned at the upper part thereof; the bionic tooth implant also comprises at least one subsidiary root; the basal platform is mounted on the main root via the basal platform part of the main root; wherein an inclined hole is provided on the basal platform; an inclined-direction hole communicated with the inclined hole is provided on the main root; the subsidiary root comprises the fixing root part positioned at the lower part thereof and a connected part positioned at the upper part thereof; the connected part is mounted in the inclined hole; the subsidiary root extends from the inclined-direction hole through the main root; and at least a part of the fixing root part is positioned at the outer part of the main root.

The invention has the following technical proposal:

Preferably, in order that the basal platform and the main root are further stably connected together to facilitate the operation, the lower part of the basal platform has at least one cylinder-shaped body extending downwards and tapering. The main root is provided with one hole therein, which accommodates the cylinder-shaped body.

Preferably, in order to facilitate convenient periphery positioning between the basal platform and the main root, a positioning part, matched with each other and used for determining the periphery position of the basal platform, is provided at the lower part of the basal platform and in the main root.

Preferably, the basal platform is provided with at least one cylinder-shaped body at the lower part thereof, which extends downwards and becomes tapering; the positioning part may be one polyhedra extending out from the lower end of the cylinder-shaped body; and the inner part of the main root is provided with a hole accommodating the cylinder-shaped body of the basal platform and a polygon hole accommodating the polyhedral of the basal platform.

Preferably, in order that the main root, the subsidiary root and the basal platform are stably connected together, the surface of the subsidiary root is provided with a thread; and the inclined hole of the basal platform also is provided with the thread matched with the thread on the surface of the subsidiary root, thus facilitating the subsidiary root and the basal platform to be stably connected together.

Preferably, the basal platform part of the main root is formed by the fixing root part of the main root integrally and upwards and provided with a specific body.

Preferably, the basal platform part of the main root is one platform formed by the upper end surface of the fixing root part of the main root.

Preferably, based on the abovementioned proposal, the cylinder-shaped body at the lower part of the basal platform continuously consists of one big cylinder-shaped body and one small cylinder-shaped body; a center through hole is formed axially at the center of the cylinder-shaped body of the basal platform; a center thread hole is provided on the place where the inner part of the main root is corresponding to the center through hole; and the screw is fixed in the center thread hole through the center through hole and connects the basal platform and the main root.

Another objective of the present is to provide a basal platform specifically used for the abovementioned bionic tooth implant. The basal platform comprises a supporting body at the upper part thereof for mounting the bionic tooth and at least one cylinder-shaped body positioned at the lower part thereof, both of which are integrated into one body; at least one positioning block or positioning groove is also formed on the outer surface of the cylinder-shaped body; and the inclined hole is obliquely formed in the inner part of the basal platform and communicated with the inner parts of a supporting body at the upper part thereof and the cylinder-shaped body at the lower part thereof.

Another objective of the present is to provide a subsidiary root specifically used for the abovementioned bionic tooth implant. The subsidiary root comprises a fixing root part positioned at the lower part thereof and a connected part positioned at the upper part thereof; and the connected part is a thread on the outer surface of the upper part of the subsidiary root.

The invention has the following effects: after the main root is implanted into the jaw of the patient, the basal platform is directly inserted into the main root and then the matched installation between the main root and the basal platform is completed. Then the subsidiary root is directly rotated into the jaw, and the integrated implanting of the bionic tooth implant is completed. The two-stage operation and the arrangement of the basal platform are not needed; therefore the whole operation process is convenient and quick.

DRAWINGS OF THE INVENTION

The invention is described through examples and drawings, wherein

EMBODIMENTS OF THE INVENTION

Figure 1:
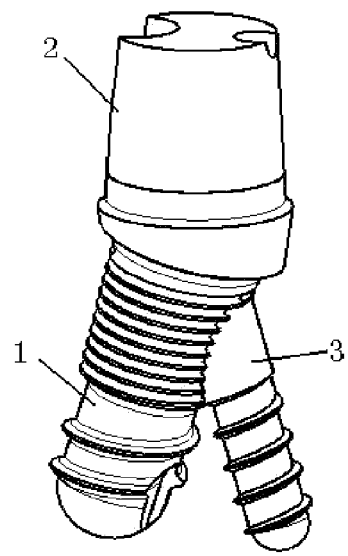
FIGS. 1-9 are schematic diagrams of Example 1 of the invention.
Figure 2:
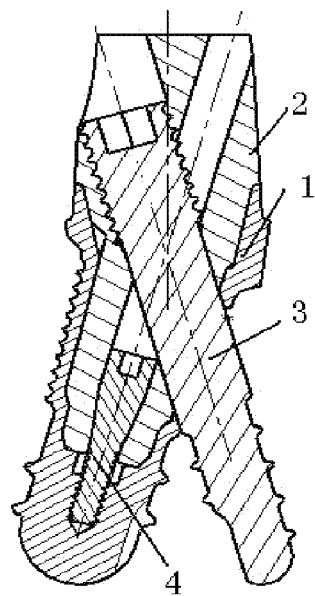
Figure 3:
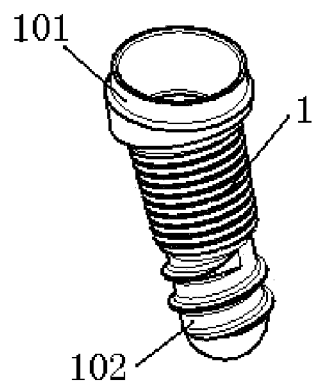
Figure 4:
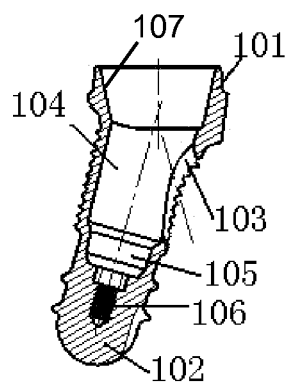

In Example 1 of the invention, as shown in FIGS. 1 and 2, a basal platform of a bionic tooth implant comprises a main root 1, a basal platform 2 and a subsidiary root 3. The detailed structures of all portions and the connecting relation between the portions are as follows:

As shown in FIGS. 3 and 4, wherein the main root 1 comprises a fixing root part 102 positioned at the lower part thereof and a basal platform part 101 positioned at the upper part thereof; the lateral wall of the main root is also provided with one inclined-direction hole 103 used for passing through the subsidiary root 3. A mounting hole used for mounting the basal platform is also provided in the main root 1. The mounting hole is one big hole and one small hole both of which are gradually tapering downwards and have taper, that is, holes 104 and 105. The bottom of the hole 105 is provided with one thread hole 106. A tapered basal platform mounting hole 107 at an upper end receives a tapered body 206 of the basal platform 2. A supporting body 207 configured for mounting a bionic tooth extends away from the tapered basal platform mounting hole 107.

Figure 5:
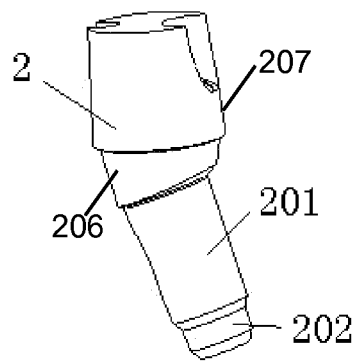
Figure 6:
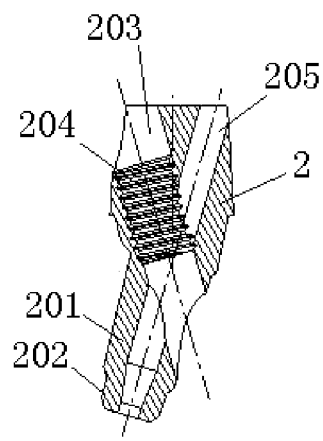
Figure 9:
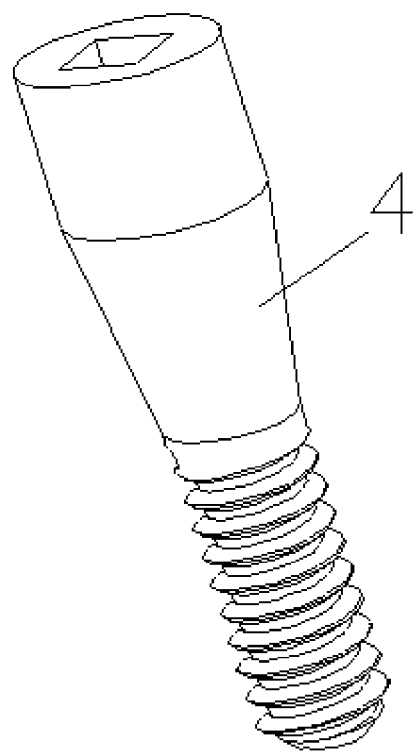

As shown in FIGS. 5 and 6, one big cylinder-shaped body and one small cylinder-shaped body are continuously connected at the lower part of the basal platform 2, that is, cylinder-shaped bodies 201 and 202. The cylinder-shaped body 201 and the hole 104 are matched with each other. The cylinder-shaped body 202 and the hole 105 are matched with each other. The basal platform 2 is also provided with the inclined hole 203 communicated with the inclined-direction hole 103 of the main root 1, and one hole 205 used for passing through a screw 4. The screw 4 is shown in FIG. 9.

Figure 7:
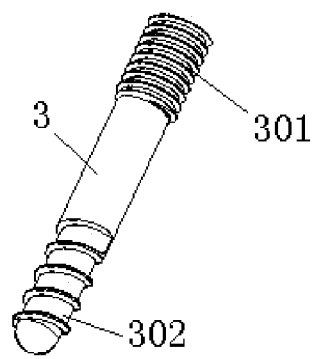
Figure 8:
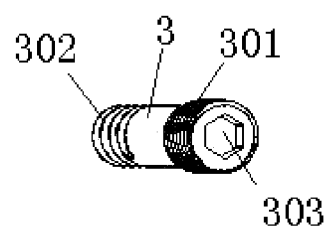

As shown in FIGS. 7 and 8, the subsidiary root 3 comprises a fixing root part 302 positioned at the lower part thereof and a connected part 301 positioned at the upper part thereof; and the top end of the connected part 301 is also provided with one inner hexagon hole 303. When the subsidiary root 3 is mounted, the subsidiary root 3 may be rotated and mounted in the basal platform 2 by an inner hexagon wrench.

The fitting relation among the main root 1, the basal platform 2 and the subsidiary root 3 is shown in FIG. 2. The cylinder-shaped bodies 201 and 202 of the basal platform 2 are placed in the holes 104 and 105. The screw 4 is positioned in the hole 205 and fixes the basal platform 2 in the main root 1. The subsidiary root 3 is mounted in the inclined hole 203 through the thread of the connected part 301 thereof, connected with the thread 204 in the inclined hole 204, and extends to the outer part of the main root 1 through the inclined-direction hole 103. The fixing root part 302 is exposed out of the main root 1.

Figure 10:
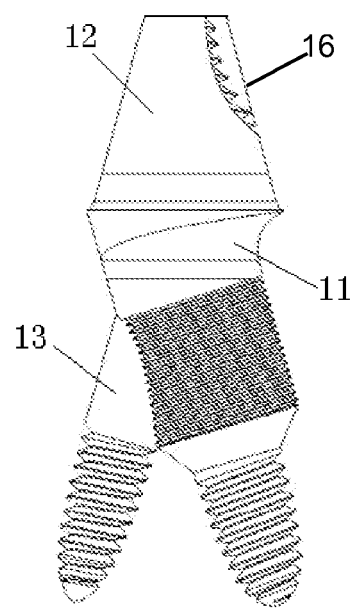
FIGS. 10-16 are schematic diagrams of Example 2 of the invention.
Figure 11:
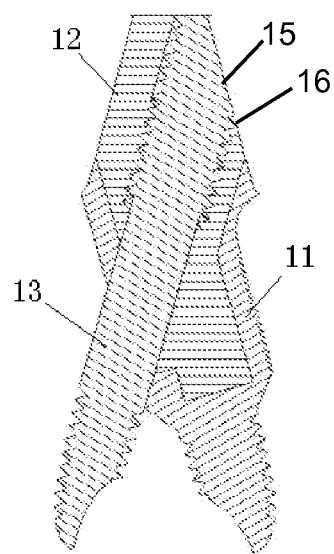
Figure 12:
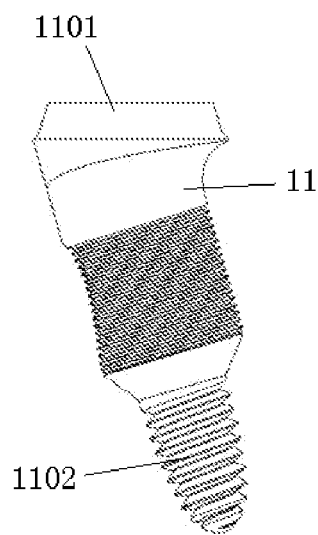
Figure 13:
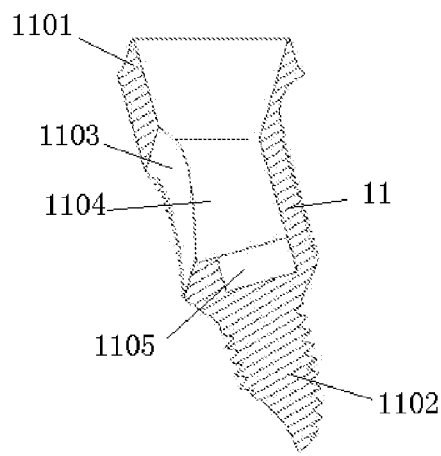

In Example 2 of the invention, as shown in FIGS. 10 and 11, a basal platform of a bionic tooth implant comprises a main root 11, a basal platform 12 and a subsidiary root 13. The detailed structures of all parts and the connecting relation between the parts are as follows:

As shown in FIGS. 12 and 13, wherein the main root 11 comprises a fixing root part 1102 positioned at the lower part thereof and a tapered basal platform part 1101 positioned at the upper part thereof. The lateral wall of the main root 11 is also provided with one inclined-direction hole 1103 used for passing through the subsidiary root 13. A mounting hole used for mounting the basal platform is also provided in the main root 11. The bottom of the mounting hole 1104 also has one polygon hole 1105 used for assisting in positioning. The polygon hole 1105 also may be used for positioning a wrench when the main root is implanted. A tapered body 1204 of the basal platform 12 abuts the tapered basal platform part 1101.

As shown in FIG. 10, the connected part 301 can be flush with the taper of basal platform supporting body 207 so that the connected part 301, when installed, does not protrude from the inclined hole 16 in the supporting body. As shown in FIG. 11, a tapered edge 15 can be included on the subsidiary root 13 so that the connected part is flush with the taper of the supporting body 207.

Figure 14:
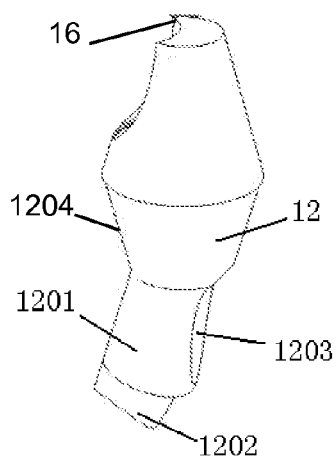
Figure 15:
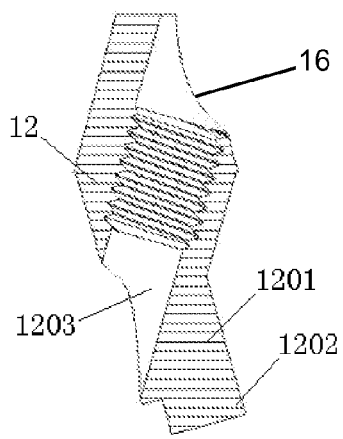

As shown in FIGS. 14 and 15, the basal platform 12 comprises a cylinder-shaped body 1201 at the lower part thereof. The cylinder-shaped body 1201 and a mounting hole 1104 are matched with each other. The bottom of the cylinder-shaped body 1201 is provided with one polyhedral 1202 used for auxiliarily positioning. The basal platform 12 is also provided with an inclined hole 1203 thereon which is communicated with the inclined-direction hole 1103 on the main root 11. One section thread in the inclined hole 1203 is used for fixing and mounting the subsidiary root 13.

Figure 16:
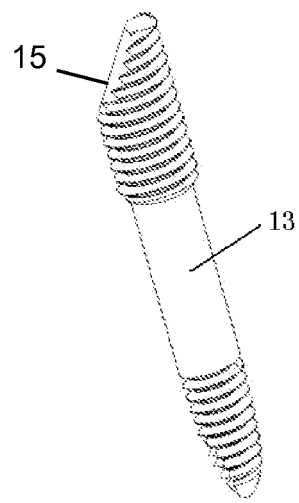

As shown in FIG. 16, the structure and form of the subsidiary root 13 is similar to those of the subsidiary root 3 in FIG. 1, which is not specified in detail. However, the subsidiary root 13 includes tapered edge 15.

When being implanted, the main root 11 is firstly implanted into the gum, and then the basal platform 12 is implanted into the main root 11. The polyhedral 1202 is implanted into a polygon hole 1105, which plays a role of peripherally positioning the platform 12, and then the subsidiary root 13 is placed into the platform. Tapered edge 15 of subsidiary root 13 aligns with basal platform inclined hole 16 to maintain the taper of the supporting body of basal platform 12.

Figure 17:
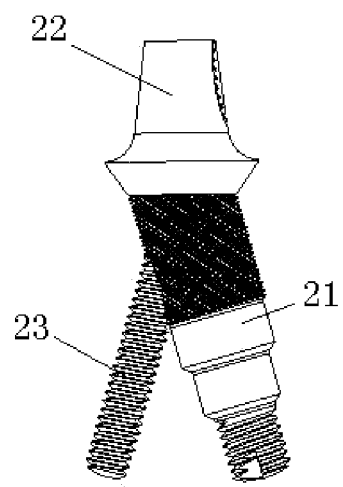
FIGS. 17-19 are schematic diagrams of Example 3 of the invention.
Figure 18:
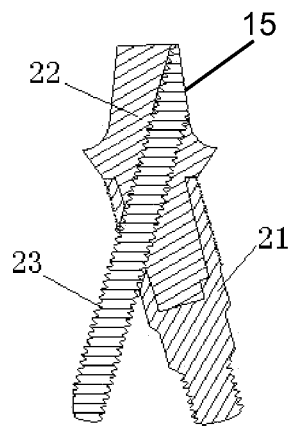
Figure 19:
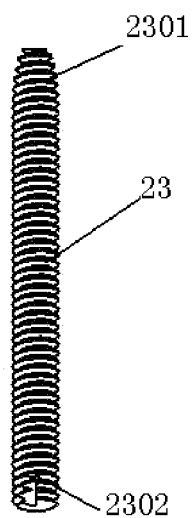

In Example 3 of the invention, as shown in FIGS. 17 and 18, a basal platform of a bionic tooth implant comprises a main root 21, a tapered basal platform supporting body 22 and a subsidiary root 23. The detailed structure and connecting relation among all portions are similar to those in Example 2, which is not specified in detail. The difference is the basal platform supporting body and the subsidiary root 23 of the main root 21, wherein the basal platform supporting body of the main root 21 is one platform formed at the upper end surface of a fixing root part of the main root 21 and does not have a definite body. The subsidiary root 23 is shown in FIG. 19. The lateral wall of the subsidiary root 23 is all provided with an outer thread from top to bottom. Its upper part is a connected part 2301, and its lower part is the fixing root part 2302. In this example, after the main root 21 and the basal platform supporting body 22 are fitted, the subsidiary root is directly rotationally placed into them. FIG. 18 illustrates that subsidiary root 13 can have tapered edge 15.

As to all of characteristics, methods or steps in the processes disclosed in the invention, in additions to mutually exclusive characteristics and/or steps, the rest can be combined in any forms.

Any one of characteristics disclosed in this specification (including any of the appended claims, abstract and drawings) may be replaced by other equivalent or alternative characteristics with similar purpose, unless specifically described. That is, unless specific description, each of the characteristics is just one example in a series of equivalent or similar characteristics.

The invention is not limited to the foregoing specific embodiment. The invention is extended to any new characteristic or new combination disclosed in this specification, as well as any new method, a step of a process or any new combination disclosed in this specification.

We claim:

1. A bionic tooth implant, comprising:
    a main root comprising:
        an exterior comprising a threaded fixing root part positioned at a lower end;
        a basal platform mounting hole at an upper end;
        a cylindrical basal platform mounting hole extending from the basal platform mounting hole into the main root;
        a polygonal mounting hole extending from the cylindrical basal platform mounting hole, the polygonal mounting hole comprising a smaller diameter than a diameter of the cylindrical basal platform mounting hole; and
        an inclined-direction hole passing through the main root from the basal platform mounting hole, through the cylindrical basal platform mounting hole in the main root, above the polygonal mounting hole, and to the exterior of the main root;
    a basal platform positioned in the main root, the basal platform comprising:
        a supporting body configured for mounting a bionic tooth, the supporting body extending away from the basal platform mounting hole;
        a cylinder-shaped body, the cylinder-shaped body positioned within the cylindrical basal platform mounting hole;
        a mounting body extending from the cylinder-shaped body in to the main root; and
        an inclined hole passing through the supporting body and through the cylinder-shaped body of the basal platform, the inclined hole passing above the mounting body; and
    a subsidiary root mounted through the inclined hole of the basal platform, through the inclined-direction hole, and extending out of the main root inclined-direction hole.

2. The bionic tooth implant of claim 1, wherein the a basal platform mounting hole at the upper end is tapered, and wherein the basal platform further comprises a tapered body, and wherein the tapered body is in the tapered basal platform mounting hole.

3. The bionic tooth implant of claim 2, wherein the cylinder-shaped body adjoins the tapered body.

4. The bionic tooth implant of claim 1, wherein cylindrical basal platform mounting hole of the main root comprises a first cylindrical basal platform mounting hole and a second cylindrical basal platform mounting hole between the basal platform mounting hole and the polygonal mounting hole, wherein the second cylindrical basal platform mounting hole comprises a diameter smaller than a diameter of the first cylindrical basal platform mounting hole, and wherein the mounting body is a second cylinder-shaped body seated in the second cylindrical basal platform mounting hole.

5. The bionic tooth implant of claim 1, wherein the mounting body is a polyhedral extension seated in the polygonal mounting hole.

6. The bionic tooth implant of claim 5, wherein the mounting body and the polygonal mounting hole are configured to determine a peripheral position of the basal platform.

7. The bionic tooth implant of claim 1, wherein the cylinder-shaped body comprises a tapering portion tapering downwardly in to the main root, and wherein the a cylindrical basal platform mounting hole comprises an accommodating taper receiving the tapering portion.

8. The bionic tooth implant of claim 1, wherein the subsidiary root comprises threading, and wherein the inclined hole comprises threading for mating with the threading on the subsidiary root.

9. The bionic tooth implant of claim 1, wherein the basal platform comprises a through hole passing within the cylinder-shaped body, wherein the main root further comprises a thread hole extending from the polygonal mounting hole, and wherein the bionic tooth implant further comprises a screw fixed through the through hole and through the thread hole.

10. The bionic tooth implant of claim 9, wherein the through hole passes through the supporting body.

11. A bionic tooth implant, comprising:
    an integrally formed basal platform comprising:
        a tapered supporting body at an upper end, the tapered supporting body configured for mounting a bionic tooth;
        an externally threaded main root fixing root part positioned at a lower end;
        an externally threaded cylinder-shaped body between the tapered supporting body and the externally threaded main root fixing part; and
        an inclined hole passing from an upper external surface of the basal platform, through the tapered supporting body, through the externally threaded cylinder-shaped body, and to an external surface of the externally threaded cylinder-shaped body at a point above the externally threaded main root fixing root part; and
    a subsidiary root comprising:
        a subsidiary root fixing part extending out of the inclined hole in the externally threaded cylinder-shaped body; and
        a connecting part extending through the inclined hole from within the tapered supporting body and through the externally threaded cylinder-shaped body, the connecting part further comprising a tapered edge for aligning with the taper of the tapered supporting body.

12. The bionic tooth implant of claim 11, wherein the at least one subsidiary root comprises threading on the subsidiary root fixing part and on the connecting part, and wherein the inclined hole comprises threading for mating with the threading on the connecting part.

13. A bionic tooth implant, comprising:
    a main root comprising:
        an exterior comprising a threaded fixing root part positioned at a lower end;
        a tapered basal platform mounting hole at an upper end;
        a cylindrical basal platform mounting hole extending from the tapered basal platform mounting hole into the main root;
        a polygonal mounting hole extending from the cylindrical basal platform mounting hole, the polygonal mounting hole comprising a smaller diameter than a diameter of the cylindrical basal platform mounting hole; and an inclined-direction hole passing through the main root from the tapered basal platform mounting hole, through the cylindrical basal platform mounting hole in the main root, and above the threaded fixing root part to the exterior of the main root;

a basal platform positioned in the main root, the basal platform comprising:
  a supporting body configured for mounting a bionic tooth, the supporting body extending away from the tapered basal platform mounting hole;
  a tapered body in the tapered basal platform mounting hole;
  a cylinder-shaped body adjoining the tapered body, the cylinder-shaped body positioned within the cylindrical basal platform mounting hole;
  a mounting body adjoining the cylinder-shaped body, the mounting body extending in to the main root; and
  an inclined hole passing through the supporting body and through the cylinder-shaped body, the inclined hole passing above the mounting body; and a subsidiary root mounted through the inclined hole of the basal platform, through the inclined-direction hole, and extending out of the main root inclined-direction hole.

14. The bionic tooth implant of claim 13, wherein cylindrical basal platform mounting hole of the main root comprises a first cylindrical basal platform mounting hole and a second cylindrical basal platform mounting hole between the basal platform mounting hole and the polygonal mounting hole, wherein the second cylindrical basal platform mounting hole comprises a diameter smaller than a diameter of the first cylindrical basal platform mounting hole, and wherein the mounting body is a second cylinder-shaped body seated in the second cylindrical basal platform mounting hole.

15. The bionic tooth implant of claim 13, wherein the mounting body is a polyhedral extension seated in the polygonal mounting hole.

16. The bionic tooth implant of claim 15, wherein the mounting body and the polygonal mounting hole are configured to determine a peripheral position of the basal platform.

17. The bionic tooth implant of claim 13, wherein the cylinder-shaped body comprises a tapering portion tapering downwardly in to the main root, and wherein the a cylindrical basal platform mounting hole comprises an accommodating taper receiving the tapering portion.

18. The bionic tooth implant of claim 13, wherein the subsidiary root comprises threading, and wherein the inclined hole comprises threading for mating with the threading on the subsidiary root.

19. The bionic tooth implant of claim 13, wherein the basal platform comprises a through hole passing within the cylinder-shaped body, wherein the main root further comprises a thread hole extending from the polygonal mounting hole, and wherein the bionic tooth implant further comprises a screw fixed through the through hole and through the thread hole.

20. The bionic tooth implant of claim 19, wherein the through hole passes through the supporting body.

* * * * *